(12) United States Patent
Keene (10) Patent No.: US 10,136,747 B2
(45) Date of Patent: Nov. 27, 2018

(54) PROTECTIVE MAT AND METHOD FOR PROTECTING A FLOOR FROM SPILLAGE AND DEBRIS

(71) Applicant: James R. Keene, Pepper Pike, OH (US)

(72) Inventor: James R. Keene, Pepper Pike, OH (US)

(73) Assignee: Keene Building Products Co., Inc., Mayfield Heights, OH (US)

( * ) Notice: Subject to any disclaimer, the term of this patent is extended or adjusted under 35 U.S.C. 154(b) by 70 days.

(21) Appl. No.: 15/308,882

(22) PCT Filed: May 6, 2015

(86) PCT No.: PCT/US2015/029384
§ 371 (c)(1),
(2) Date: Nov. 4, 2016

(87) PCT Pub. No.: WO2015/171706
PCT Pub. Date: Nov. 12, 2015

(65) Prior Publication Data
US 2017/0071389 A1    Mar. 16, 2017

Related U.S. Application Data

(60) Provisional application No. 61/989,079, filed on May 6, 2014.

(51) Int. Cl.
*A47G 27/02* (2006.01)
*B32B 27/12* (2006.01)
(Continued)

(52) U.S. Cl.
CPC ........ *A47G 27/0206* (2013.01); *A47L 23/266* (2013.01); *B32B 5/022* (2013.01);
(Continued)

(58) Field of Classification Search
CPC ............ A47G 27/0206; A47G 27/0231; A47L 23/266; C09J 7/045; C09J 2400/263;
(Continued)

(56) References Cited

U.S. PATENT DOCUMENTS 4,609,580 A * 9/1986 Rockett ............. A47G 27/0206
428/198
4,900,377 A 2/1990 Redford et al.
(Continued)

FOREIGN PATENT DOCUMENTS

DE       19523494      1/1997
DE     102005037662    2/2007
(Continued)

OTHER PUBLICATIONS

International Search Report and Written Opinion for corresponding International Application No. PCT/US2015/029384 dated Aug. 27, 2015.
International Preliminary Report on Patentability for corresponding International Application No. PCT/US2015/029384 dated Aug. 8, 2016.
Written Opinion of the International Preliminary Examining Authority for corresponding International Application No. PCT/US2015/029384 dated Apr. 18, 2016.
(Continued)

*Primary Examiner* — Patricia L. Nordmeyer
(74) *Attorney, Agent, or Firm* — Renner, Otto, Boisselle & Sklar, LLP (57) ABSTRACT

The present disclosure provides a protective mat and a method for protecting a floor from spillage, debris and/or scratches. The protective mat may also provide other advantages such as impact resistance and/or reduction of foot/leg fatigue. The protective mat includes a web of extruded polymer monofilaments. The protective mat may further include a membrane. The membrane may be made of a
(Continued)

liquid impermeable material. The method includes overlaying a portion of a floor with the protective mat.

15 Claims, 5 Drawing Sheets

(51) Int. Cl.
| | |
|---|---|
| *B32B 7/06* | (2006.01) |
| *B32B 7/12* | (2006.01) |
| *D04H 3/16* | (2006.01) |
| *B32B 5/02* | (2006.01) |
| *A47L 23/26* | (2006.01) |
| *C09J 7/04* | (2006.01) |
| *A61B 50/10* | (2016.01) |

(52) U.S. Cl.
CPC ............... *B32B 7/06* (2013.01); *B32B 7/12* (2013.01); *B32B 27/12* (2013.01); *C09J 7/045* (2013.01); *D04H 3/16* (2013.01); *A47G 27/0231* (2013.01); *A61B 50/10* (2016.02); *B32B 2262/0238* (2013.01); *B32B 2262/0253* (2013.01); *B32B 2262/0276* (2013.01); *B32B 2262/062* (2013.01); *B32B 2307/558* (2013.01); *B32B 2307/748* (2013.01); *B32B 2571/00* (2013.01); *C09J 2400/263* (2013.01)

(58) Field of Classification Search
CPC .. D04H 3/16; B32B 5/022; B32B 7/06; B32B 7/12; B32B 27/12; B32B 2262/0238; B32B 2262/0253; B32B 2262/0276; B32B 2262/062; B32B 2307/558; B32B 2307/748; B32B 2571/00; A61B 50/10
See application file for complete search history.

(56) References Cited

U.S. PATENT DOCUMENTS

| | | |
|---|---|---|
| 2002/0164465 A1 | 11/2002 | Curro et al. |
| 2004/0265534 A1 | 12/2004 | Curro et al. |
| 2006/0037692 A1 | 2/2006 | Plaskett et al. |
| 2009/0095400 A1 | 4/2009 | Stelter et al. |
| 2011/0107700 A1 | 5/2011 | Keene |
| 2012/0121849 A1 | 5/2012 | Nojima |
| 2012/0183744 A1 | 7/2012 | Keene |

FOREIGN PATENT DOCUMENTS

| | | |
|---|---|---|
| DE | 102009001059 | 8/2010 |
| EP | 1657334 | 5/2006 |
| WO | 2004038078 | 5/2004 |
| WO | 2009127819 | 10/2009 |
| WO | 2014179293 | 11/2014 |

OTHER PUBLICATIONS

Reply to International Search Report and Written Opinion for corresponding International Application No. PCT/US2015/029384 dated Mar. 7, 2016.
Reply to Written Opinion of the International Preliminary Examining Authority for corresponding International Application No. PCT/US2015/029384 dated Jun. 16, 2016.

* cited by examiner

PROTECTIVE MAT AND METHOD FOR PROTECTING A FLOOR FROM SPILLAGE AND DEBRIS

This application is a national phase of International Application No. PCT/US2015/029384 filed May 6, 2015 and published in the English language, which claims priority to U.S. Provisional Application No. 61/989,079 filed on May 6, 2014. These applications are incorporated herein by reference in their entirety.

TECHNICAL FIELD

The present disclosure relates generally to protecting a floor, more particularly to a protective mat and method for protecting a floor from spillage and debris that includes a web of extruded polymer monofilaments.

BACKGROUND

Protective sheets, such as drop cloths and tarps, are commonly used by painters to protect surfaces from, for example, paint spills, drips, splattering and overspray. Similar sheets are used in operating rooms to allow for easy disposal of bodily fluids and surgical debris.

SUMMARY

The present disclosure provides a protective mat and a method for protecting a floor from spillage, debris and/or scratches. The protective mat may also provide other advantages such as impact resistance and/or reduction of foot/leg fatigue. The protective mat includes a web of extruded polymer monofilaments. The protective mat may further include a membrane. The membrane may be made of a liquid impermeable material. The method includes overlaying a portion of a floor with the protective mat.

In accordance with one aspect of the present disclosure, a protective mat includes: a web of extruded polymer monofilaments, the polymer monofilaments being heat welded at junctions to form a matrix of tangled monofilaments, the web having a top surface, a bottom surface and a plurality of side surfaces extending from the top surface to the bottom surface; and a membrane underlaying at least a portion of the bottom surface of the web, the membrane having a top surface, a bottom surface and a plurality of side surfaces extending from the top surface to the bottom surface.

In one embodiment, the web has a thickness in the range of 0.0625 inch to 0.375 inch.

In another embodiment, the membrane is affixed to the bottom surface of the web.

In another embodiment, the membrane comprises a nonwoven fabric, canvas, polyester, cotton, rubber, polyvinyl chloride, polyethylene, bitumen, or a mixture of two or more thereof.

In another embodiment, the mat includes a plurality spacer elements projecting upwardly away from the top surface of the web.

In another embodiment, the plurality of spacer elements are formed from the same material as the web.

In another embodiment, the mat further includes at least one dam extending along at least one of the side surfaces of the web, the dam projecting downwardly from the top surface of the web towards the bottom surface of the web.

In another embodiment, the mat further includes at least one bump extending along at least one of the side surfaces of the web, the bump projecting upwardly away from the top surface of the web.

In another embodiment, the mat further includes at least one binding strip contacting the top surface of the web and extending along at least at least one of the side surfaces of the web, or contacting the bottom surface of the membrane and extending along at least one of the side surfaces of the membrane.

In accordance with another aspect of the present disclosure, a protective mat includes: a web of extruded polymer monofilaments, the polymer monofilaments being heat welded at junctions to form a matrix of tangled monofilaments, the web having a top surface, a bottom surface and a plurality of side surfaces extending from the top surface to the bottom surface; and a pressure sensitive adhesive on at least one of the top and bottom surfaces.

In one embodiment, the mat further includes a release layer covering the pressure sensitive adhesive.

In accordance with yet another aspect of the present disclosure, a method for protecting a floor from spillage and debris includes: overlaying a portion of the floor with a protective mat, the protective mat including a web of extruded polymer monofilaments, the polymer monofilaments being heat welded at junctions to form a matrix of tangled monofilaments, the web having a top surface, a bottom surface and a plurality of side surfaces extending from the top surface to the bottom surface.

In one embodiment, the method includes overlaying a portion of the floor with a membrane, the membrane comprising a nonwoven fabric, canvas, polyester, cotton, rubber, polyvinyl chloride, polyethylene, bitumen, or a mixture of two or more thereof.

In another embodiment, the protective mat further includes a membrane overlaying the bottom surface of the web, the membrane comprising a high-loft nonwoven fabric, canvas, polyester, cotton, rubber, polyvinyl chloride, polyethylene, bitumen, or a mixture of two or more thereof.

In another embodiment, the protective mat further includes at least one binding strip contacting the top surface or the bottom surface of the web and extending along at least one of the side surfaces of the web.

In another embodiment, the method further includes forming the protective mat into a roll and the floor is overlaid with the protective mat by rolling out the roll onto the floor such that the bottom surface of the web contacts the floor.

In another embodiment, the web has a thickness in the range of 0.0625 inch to 0.375 inch.

In another embodiment, the mat includes a plurality spacer elements projecting upwardly away from the top surface of the web.

In another embodiment, the mat further includes at least one dam along at least one of the side surfaces of the web, the dam projecting downwardly from the top surface towards the bottom surface.

In another embodiment, the mat further includes at least one bump along at least one of the side surfaces of the top surface of the web, the bump projecting upwardly away from the top surface of the web.

The foregoing and other features of the disclosure are hereinafter described in greater detail with reference to the accompanying drawings.

DETAILED DESCRIPTION

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

An exemplary protective mat includes a web of extruded polymer monofilaments and a membrane. The polymer monofilaments are heat welded at junctions to form a matrix of tangled monofilaments. The protective mat is overlaid onto a floor to protect the floor from spillage and debris.

Figure 1:
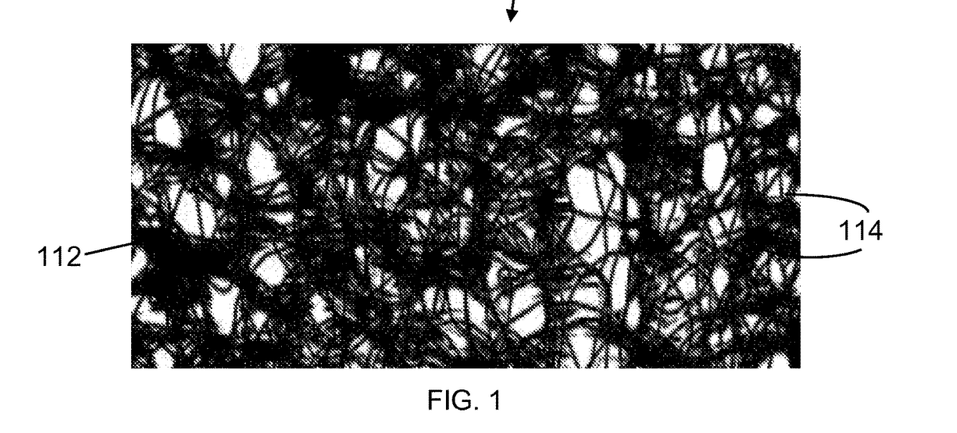
FIG. 1 is a plan view of an exemplary protective mat according to the disclosure.

Referring now in detail to the drawings, and initially to FIG. 1, an exemplary protective mat is shown at 110. The mat includes a web 112 of extruded polymer monofilaments 114. The monofilaments 114 are heat welded at junctions to form a matrix of tangled monofilaments 114. The monofilaments of the web 112 may be made from any thermoplastic polymer that provides the desired properties of flexibility and resiliency when included in the mat 110. The monofilaments 114 may be made of polyolefin (e.g., polyethylene, polypropylene, etc.), polyamide (e.g., Nylon), polyester, polyvinylhalide (e.g., polyvinylchloride (PVC), polyvinylidene chloride, polyvinyltetrafluoride, or polyvinylchlorotrifluoride), polystyrene, polyvinylester (e.g., polyvinyl acetate, etc.), or a mixture of two or more thereof.

The monofilaments 114 are extruded onto a substrate having the desired structural profile to form the web 112. The web 112 is preferably constructed in accordance with techniques well known to one of ordinary skill in the art, such as disclosed by, for example, U.S. Pat. Nos. 3,687,759; 3,691,004; and 4,212,692, the contents of all of which are hereby incorporated by reference in their entireties. Due to its filamentatious structure, the web 112 contains a great number of mutually interconnected voids that allow gases and liquid to flow freely therethrough.

In one example, the monofilaments 114 may have an average diameter in the range of 0.25 mil to 6 mils, or in another example in the range of 0.50 mil to 5 mils, or in another example in the range of 0.75 mil to 4.5 mils, or in another example in the range of 1 mil to 4 mils.

The density of the mat is influenced by the diameter of the monofilaments 114. Thinner filaments generally form a relatively denser web 112. As the diameter of the monofilaments 114 is increased, the density of the web 112 decreases and results in a more open structure. In one example, the web 112 may include less than 50% void in relation to the entire volume of the web 112. In another example, the web 112 may include a void amount in the range of 50% to 75% void in relation to the entire volume of the web 112. In yet another example, the web 112 may include greater than 75% void in relation to the entire volume of the web 112.

The thickness of the web 112 may be increased or decreased for accommodating different amounts of a spill. For example, a web 112 required to contain a five gallon bucket of paint may be thicker than a web 112 required to contain surgical debris during a surgery.

In one example, the thickness of the web 112 may be in the range of 1 inch to 10 inches, or in another example in the range of 4 inches to 7 inches. In another example, the thickness of the web 112 may be in the range of 0.1 inch to 1 inch, or in another example, in the range of 0.4 inch to 0.7 inch. In yet another example, the thickness of the web 112 may be in the range of 0.05 inch to 0.5 inch, or in another example, in the range of 0.0625 inch to 0.375 inch. In a preferred embodiment, the thickness of the web is 0.125 inch.

The resilience or flexibility of the mat 110 may be increased or decreased to prevent strain in the leg muscles of painters who otherwise are standing on hard surfaces for long periods of time. The resilience may be varied by varying the density of the monofilaments in the web and/or the thickness of the web.

Figure 2:
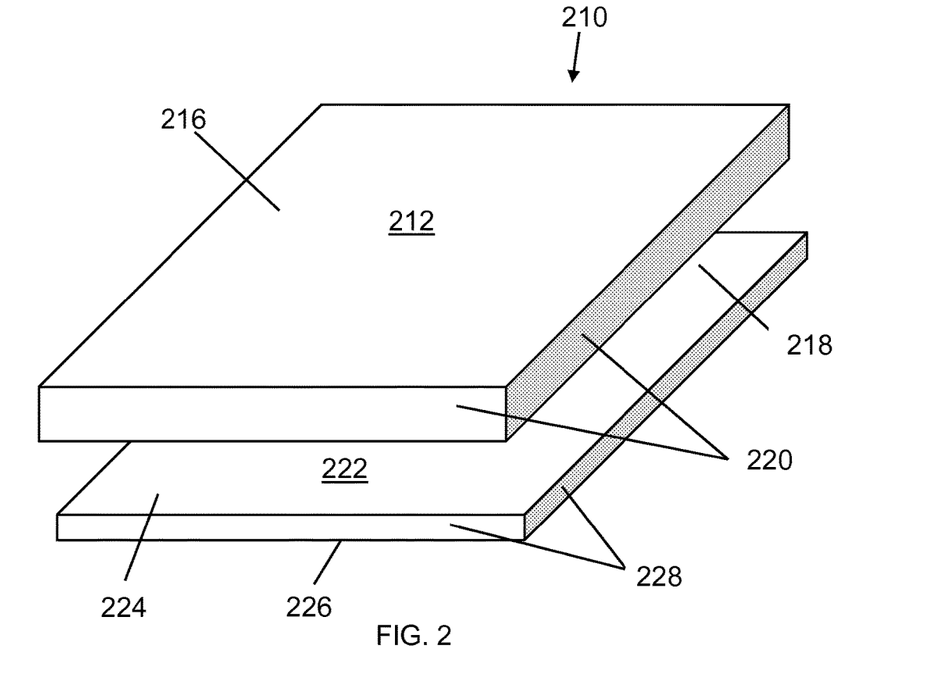
FIG. 2 is a perspective view of an embodiment of the device of FIG. 1, wherein the mat includes a membrane.

Referring now to FIG. 2, the web 212 has a top surface 216, a bottom surface 218 and a plurality of side surfaces 220 extending from the top surface 216 to the bottom surface 218.

As shown, the protective mat 210 may further include a membrane 222 underlaying at least a portion of the bottom surface 218 of the web 212, as would be preferred in many applications. The membrane 222 has a top surface 224, a bottom surface 226 and a plurality of side surfaces 228 extending from the top surface 224 to the bottom surface 226. The membrane 222 may be made of a nonwoven fabric, canvas, polyester, cotton, rubber, polyvinyl chloride, polyethylene, bitumen, or a mixture of two or more thereof. The use of a moisture resistant or impervious fabric, such as rubber, polyvinyl chloride, polyethylene or bitumen allows for the membrane 222 to be very thin. This reduces the weight of the protective mat 210, which provides an advantage over other applications of floor protection.

The membrane 222 may have a coating with a slip resistant quality, such as a resin coating.

In one example, the thickness of the membrane 212 is less than 5% of the thickness of the web 212. In another example, the thickness of the membrane 212 is in the range of 5% to 50% of the thickness of the web 212, or in another example, in the range of 10% to 25% of the thickness of the web 212. In yet another example, the thickness of the membrane 212 is greater than 50% of the thickness of the web 212.

In some embodiments, the membrane 222 is attached to the web 212. The membrane 222 may be attached to the web 212 by adhesive, welding, nails, staples or other suitable means.

Figure 3:
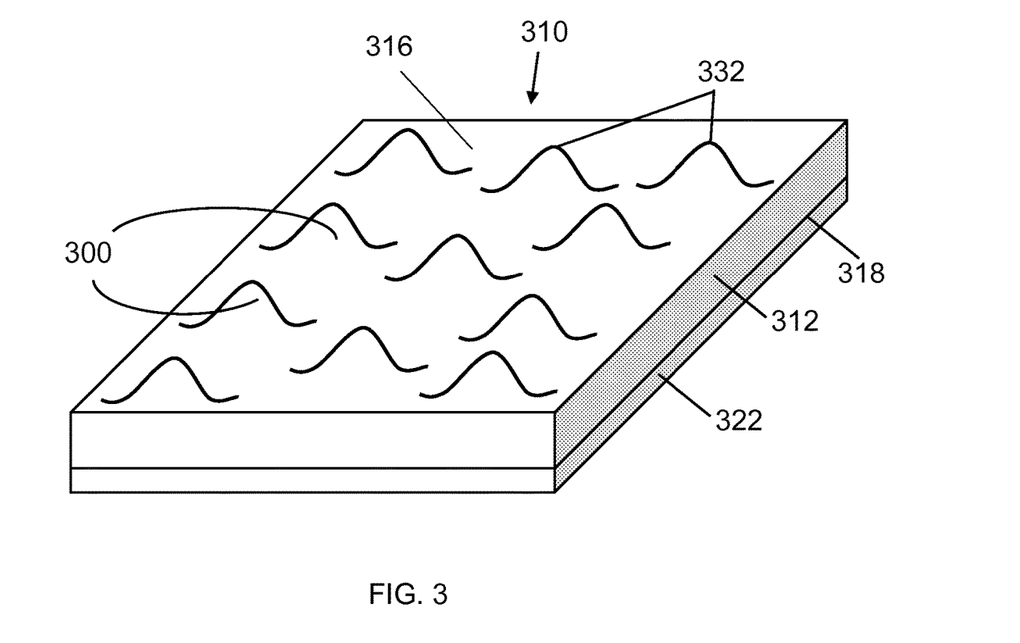
FIG. 3 is a perspective view of another embodiment of the device of FIG. 1, wherein the mat includes a plurality of spacer elements.

Referring now to FIG. 3, the mat 310 includes a plurality of spacer elements 330 projecting upwardly away from the top surface 316 of the web 312. Each spacer element 330 has a top surface 332 at the apex of the spacer element 330. The top surfaces 332 of the plurality of spacer elements 330 create a contact area, which is defined as a plane of the top surfaces 332 of the spacer elements 330 on which a person may stand or walk opposite the underlying membrane 322.

Decreasing the amount of contact surface decreases the chances of tracking any liquid off of the mat 310. For example, the percentage of space that a shoe would need to support a 200 pound person may be 2% to 15% of the top surfaces 332 of the plurality of spacer elements 330, leaving 85% to 98% of the top surfaces 332 void. This decreases the chances of tracking any liquid off of the mat 310 than if a high percentage like 25% or more of the top surfaces 224 was walked upon.

In one embodiment, the top surfaces 332 provide a contact surface less than 25%, based on the total area covered by the mat 310. In another embodiment, the top surfaces 332 provide a contact surface of less than 10%. In yet another embodiment, the top surfaces 332 provide a contact surface of less than 5%.

As depicted, the plurality of spacer elements 330 form a peak and valley pattern. However, the plurality of spacer elements 330 may form any geometric pattern to allow for gravity to flow the liquid to the bottom surface 318 of the web 312 while maintaining an adequate amount of contact area to suspend a shoed foot. That is, the protrusions support the person's shoes/feet above the balance of the top surface of the web 312.

The plurality of spacer elements 330 may be aligned in an alternating format as shown or may be aligned into an array of rows. The plurality of spacer elements 330 may be any geometric shape, such as cones, truncated cones, pyramids having polygonal bases, truncated pyramids having polygonal bases, cylinders, prisms or spherical units.

In one example, the height of the spacer elements 330 may be in the range of 0.1 inch to 10 inches, or in another example, in the range of 0.25 inch to 5 inches. In another example, the height of the spacer elements 330 may be in the range of 0.5 inch to 2.5 inches, or in another example in the range of 0.75 inch to 1.5 inches.

In one example, the distance between any two spacer elements 330 may be in the range of 0.1 inch to 5 inches, or in another example, in the range of 0.25 inch to 2.5 inches. In another example, the distance between any two spacer elements 330 may be in the range of 0.5 inch to 1.5 inches, or in another example, in the range of 0.75 inch to 1 inch.

In one example, the spacer elements 330 are formed from the same material as the web 312. In another example, the spacer elements 330 are formed from a separate material from the web 312 and the separate material is attached to the web 312.

Figure 4:
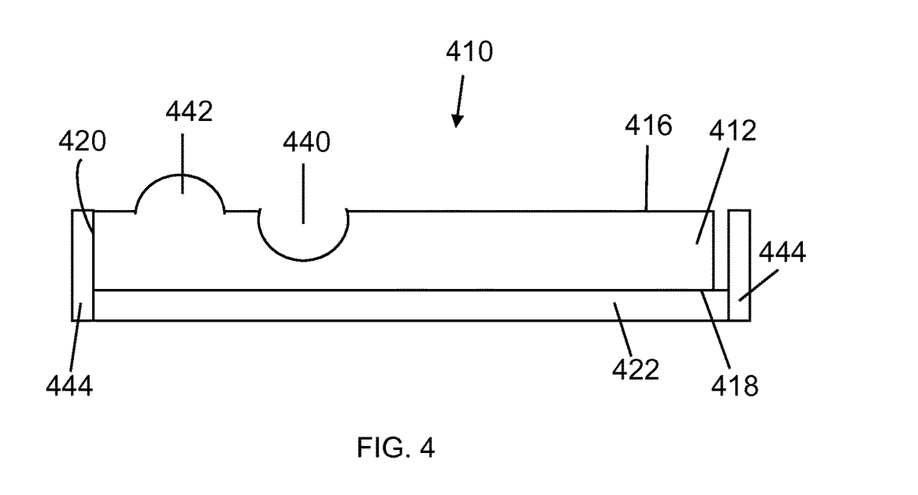
FIG. 4 is cross-sectional view of another embodiment of the device of FIG. 1, wherein the mat includes a dam and a bump.
Figure 5:
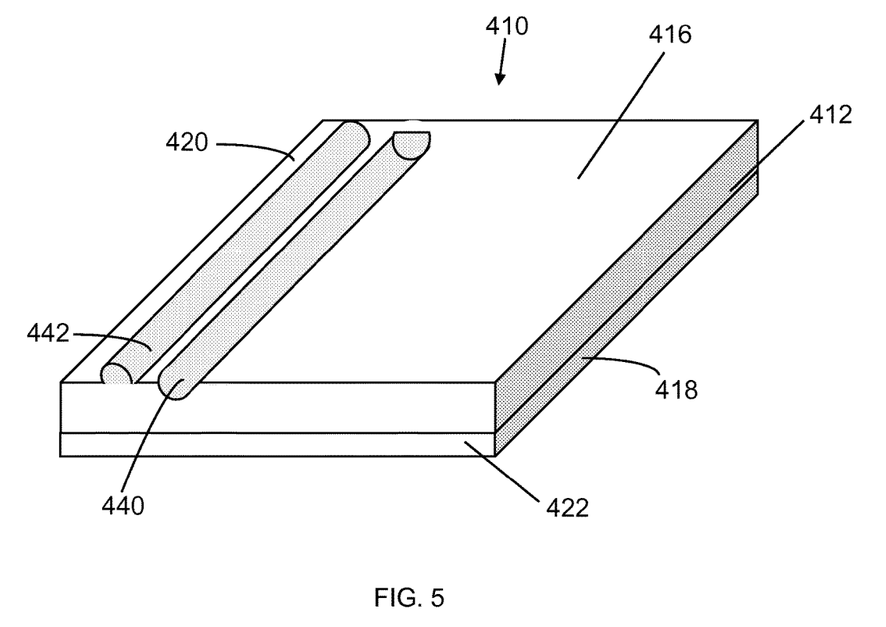
FIG. 5 is a perspective view of the embodiment shown in FIG. 4.

Referring now to FIGS. 4 and 5, another mat 410 may include at least one dam 440 extending along at least one of the side surfaces 420 of the web 412. The dam 440 projects downwardly from the top surface 416 of the web 412 towards the bottom surface 418 of the web 412. Spills, especially with thicker liquids (e.g., paint or blood) will tend to stay in place because of the surface tension. However, if the spill occurs near the edge of the mat 410, the dam 440 would hold the liquid inside the web 412.

In one example, the dam 440 may have a depth in the range 0.05 inch to 0.35 inch, or in another example, in the range of 0.1 inch to 0.2 inch.

Also as shown, the mat 410 includes at least one bump 442 extending along at least one of the side surfaces 420 of the top surface 416 of the web 412. The bump 442 projects upwardly away from the top surface 416 of the web 412. If a spill occurs near the edge of the mat 410, the bum 412 would contain the liquid within the web 412.

In one example, the bump 442 may have a height in the range of 0.1 inch to 0.75 inch, or in another example, in the range of 0.25 inch to 0.5 inch.

Though the dam 440 and bump 442 are depicted as extending along at least one of the side surfaces 420 of the top surface 416 of the web 412, the dam 440 and bump 442 may be located anywhere on the top surface 416 of the web 412 to hold and contain liquid, such as towards the center of the web 412. In particular, the dam 440 and the bump 442 may extend along the periphery of the web 412.

As also shown in FIG. 4 (but not in FIG. 5), the mat 410 may be provided at its peripheral edges with containment wall 444 that is impervious to liquid. The wall 444 may be tape adhered to the sides of the mat 410 to contain any liquid spilled on the mat 410 and prevent it from flowing off the mat 410. The wall 444 may be part of the membrane 422 that extends past the side surfaces 420 of the web 412 and is adhered to the side surfaces of the web 412 to form a tray-like containment structure.

Figure 6:
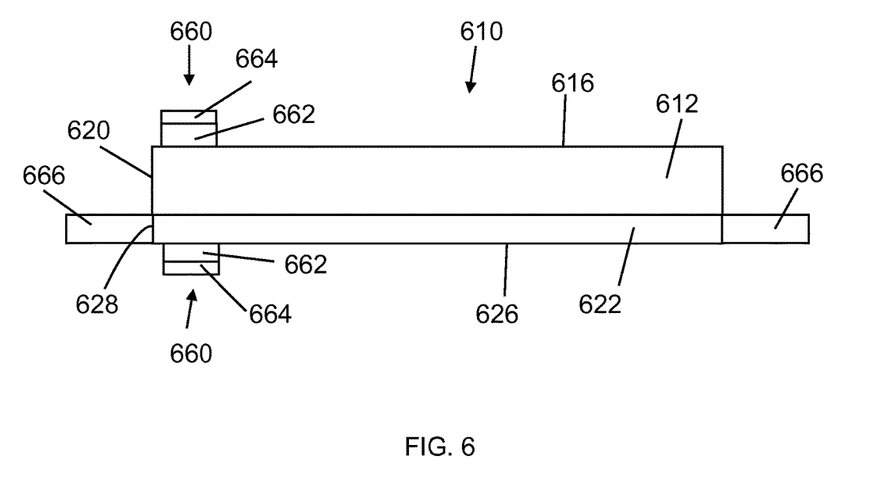
FIG. 6 is a cross-sectional view of another embodiment of the device of FIG. 1, wherein the mat includes at least one binding strip.
Figure 7:
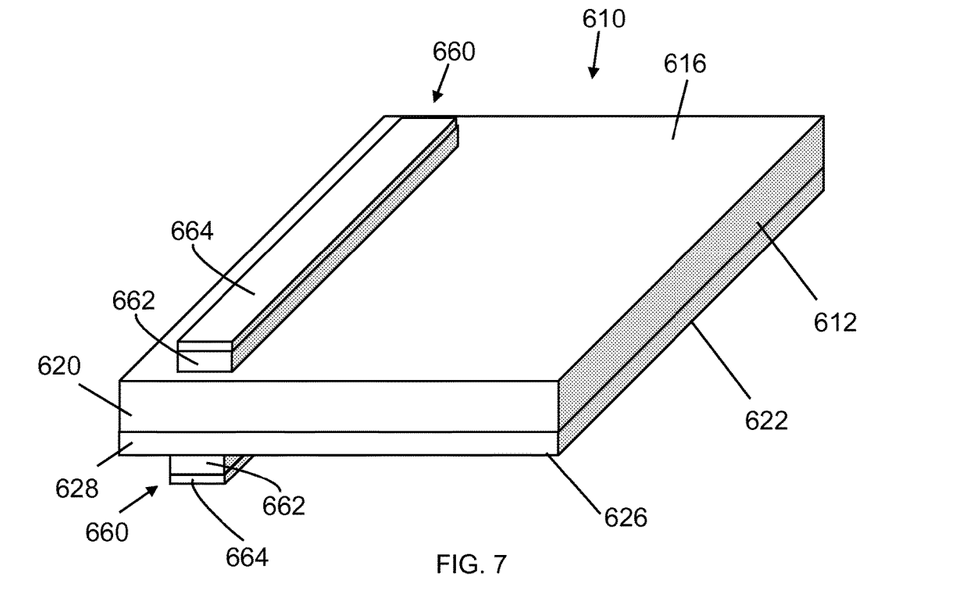
FIG. 7 is a perspective view of the embodiment shown in FIG. 6.

Referring now to FIGS. 6 and 7, another mat 610 may include at least one binding strip 660 attached to the top surface 616 of the web 612 and extending along at least one of the side surfaces 620 of the web 612, or contacting the bottom surface 626 of the membrane 622 and extending along at least one of the side surfaces 628 of the membrane 622. As depicted, the mat 610 includes one binding strip 660 contacting the top surface 616 of the web 612 and extending along at least one of the side surfaces 620 of the web 612 and one binding strip 660 contacting the bottom surface 626 of the membrane 622 and extending along at least one of the side surfaces 628 of the membrane 622. The binding strip 660 secures the protective mat 610 to the surface to be protected.

The binding strip 660 may include a pressure sensitive adhesive 662 having a release liner 664 to protect the adhesive 662 until the mat 610 is ready for use.

Though the binding strips 660 are depicted as extending along at least one of the side surfaces 620 of the web 612 and extending along at least one of the side surfaces 628 of the membrane 622, the binding strip 660 may be located anywhere on the protective mat 610 where securing is necessary, such as towards the center of the top surface 616 of the web 612 or the center of the bottom surface 626 of the membrane 622.

As shown in FIG. 6 (but not in FIG. 7), the mat 610 may include an absorptive pad 666 near the side surfaces 620 and 628 to enable wiping off support elements removed from or exiting the central portion of the mat 610, such as feet, shoes, painting equipment or ladder pads. In other embodiments, the absorptive pad 666 may be part of the membrane 622 that extends beyond the side surfaces 620 of the web 612.

Figure 8:
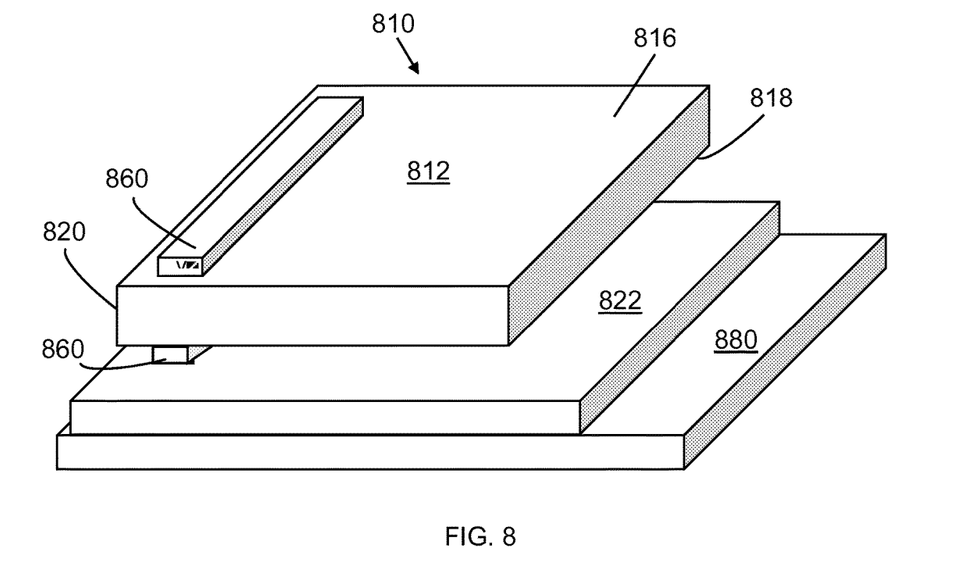
FIG. 8 is a perspective view of a protective mat included in a method for protecting a floor from spillage and debris.

Referring now to FIG. 8, a method for using the protective mat 810 for protecting a floor 880 from spillage and debris includes overlaying a portion of the floor 880 with the protective mat 810. Because the properties of the protective mat 810, the web 812 and the membrane 822 are the same as that of the protective mat, the web and the membrane described in relation to FIGS. 1-7, a full description here will be omitted.

As discussed above, the protective mat 810 may include the web 812 or the protective mat 810 may include the web 812 and the membrane 822. In embodiments where the protective mat 810 includes the web 812 and excludes the membrane 822 (e.g., FIG. 1), a separate membrane 822 may be overlaid onto a portion of the floor. Then, the protective mat 810 may be overlaid onto the membrane 822.

The protective mat 810 may further include at least one binding strip 860 contacting the top surface 816 or the bottom surface 818 of the web 812 and extending along at least one of the side surfaces 820 of the web 812. As depicted, the protective mat 810 includes one binding strip 860 contacting the top surface 816 of the web 812 and extending along at least one of the side surfaces 820 of the web 812 and one binding strip 860 contacting the bottom surface 818 of the web 812 and extending along at least one of the side surfaces 820 of the web 812. The binding strip 860 secures the web 812 to the membrane 822 or the floor 880.

Figure 9:
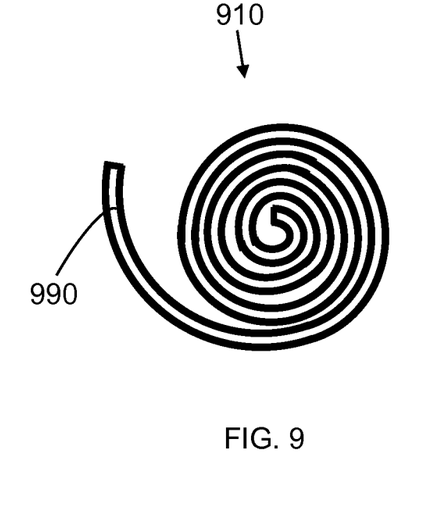
FIG. 9 is a perspective view of the protective mat shown in FIG. 8, wherein the mat is formed into a roll.

Referring now to FIG. 9, the method further includes forming the protective mat 910 into a roll 990. The floor (FIG. 8) may be overlaid with the protective mat 910 by rolling out the roll 990 onto the floor such that the bottom surface (FIG. 8) of the web 910 contacts the floor. In some embodiments, the mat 910 may include a zip strip edge (not shown) to bond two rolls 990 side by side.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A protective floor mat comprising:
a web of extruded polymer monofilaments, the polymer monofilaments being heat welded at junctions to form a matrix of tangled monofilaments, the web having a top surface, a bottom surface and a plurality of side surfaces extending from the top surface to the bottom surface, the web including a void amount of at least 50% in relation to the entire volume of the web; and
an impervious membrane underlaying at least a portion of the bottom surface of the web, the membrane having a top surface, a bottom surface and a plurality of side surfaces extending from the top surface to the bottom surface, wherein
the mat includes at least one of a dam projecting downwardly from the top surface of the web towards the bottom surface of the web and extending along at least one of the side surfaces of the web, and a bump projecting upwardly away from the top surface of the web and extending along at least one of the side surfaces of the web.

2. The mat of claim 1, wherein the web has a thickness in the range of 0.0625 inch to 0.375 inch.

3. The mat of claim 1, wherein the impervious membrane is affixed to the bottom surface of the web.

4. The mat of claim 1, wherein the impervious membrane comprises a nonwoven fabric, canvas, polyester, cotton, rubber, polyvinyl chloride, polyethylene, bitumen, or a mixture of two or more thereof.

5. The mat of claim 1, wherein the mat includes a plurality spacer elements projecting upwardly away from the top surface of the web.

6. The mat of claim 5, wherein the plurality of spacer elements are formed from the same material as the web.

7. The mat of claim 1, wherein the mat further includes at least one binding strip contacting the top surface of the web and extending along at least at least one of the side surfaces of the web, or contacting the bottom surface of the impervious membrane and extending along at least one of the side surfaces of the impervious membrane.

8. A protective floor mat comprising:
a web of extruded polymer monofilaments, the polymer monofilaments being heat welded at junctions to form a matrix of tangled monofilaments, the web having a top surface, a bottom surface and a plurality of side surfaces extending from the top surface to the bottom surface, the web including a void amount of at least 50% in relation to the entire volume of the web; and
a pressure sensitive adhesive on at least one of the top and bottom surfaces, wherein
the mat includes at least one of a dam projecting downwardly from the top surface of the web towards the bottom surface of the web and extending along at least one of the side surfaces of the web, and a bump projecting upwardly away from the top surface of the web and extending along at least one of the side surfaces of the web.

9. The mat of claim 8, further including a release layer covering the pressure sensitive adhesive.

10. A method for protecting a floor from spillage and debris, the method comprising:
overlaying a portion of the floor with a protective mat, the protective mat including a web of extruded polymer monofilaments and an impervious membrane, the polymer monofilaments being heat welded at junctions to form a matrix of tangled monofilaments, the web having a top surface, a bottom surface and a plurality of side surfaces extending from the top surface to the bottom surface, the web including a void amount of at least 50% in relation to the entire volume of the web, the mat including at least one of a dam projecting downwardly from the top surface of the web and extending along at least one of the side surfaces of the web, and a bump projecting upwardly from the top surface of the web and extending along at least one of the side surfaces of the web, the impervious membrane underlaying at least a portion of the bottom surface of the web, the impervious membrane having a top surface, a bottom surface and a plurality of side surfaces extending from the top surface to the bottom surface.

11. The method of claim 10, wherein the impervious membrane includes a nonwoven fabric, canvas, polyester, cotton, rubber, polyvinyl chloride, polyethylene, bitumen, or a mixture of two or more thereof.

12. The method of claim 10, wherein the protective mat further includes at least one binding strip contacting the top surface or the bottom surface of the web and extending along at least one of the side surfaces of the web.

13. The method of claim 10, further including forming the protective mat into a roll and the floor is overlaid with the protective mat by rolling out the roll onto the floor such that the bottom surface of the impervious membrane contacts the floor.

14. The method of claims 10, wherein the web has a thickness in the range of 0.0625 inch to 0.375 inch.

15. The method of claim 10, wherein the mat includes a plurality spacer elements projecting upwardly away from the top surface of the web.

\* \* \* \* \*

UNITED STATES PATENT AND TRADEMARK OFFICE
CERTIFICATE OF CORRECTION

PATENT NO. : 10,136,747 B2
APPLICATION NO. : 15/308882
DATED : November 27, 2018
INVENTOR(S) : James R. Keene Page 1 of 1

It is certified that error appears in the above-identified patent and that said Letters Patent is hereby corrected as shown below:

In the Specification

Summary, Column 2, Line 3 should read -- "extending along at least one of the side surfaces of"

In the Claims

Column 8, Line 12, Claim 7 should read -- "and extending along at least one of the side surfaces"

Signed and Sealed this
Twenty-sixth Day of February, 2019

Andrei Iancu
*Director of the United States Patent and Trademark Office*